(12) United States Patent
Oh et al.

(10) Patent No.: US 9,375,456 B2
(45) Date of Patent: Jun. 28, 2016

(54) **ANTIVIRAL COMPOSITION CONTAINING AN *ALEURITES FORDII* OR *DAPHNE KIUSIANA* EXTRACT OR A FRACTION THEREOF AS AN ACTIVE INGREDIENT**

(75) Inventors: Sei-Ryang Oh, Daejeon (KR); Jae Wha Kim, Daejeon (KR); Hyeong-Kyu Lee, Daejeon (KR); Kyung Seop Ahn, Daejeon (KR); Doo Young Kim, Daejeon (KR); Jung Hee Kim, Daejeon (KR); Jae Sung Song, Daejeon (KR); Ho-Bum Kang, Daejeon (KR); Inpyo Choi, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 1093 days.

(21) Appl. No.: 13/505,727

(22) PCT Filed: Nov. 3, 2010

(86) PCT No.: PCT/KR2010/007724
§ 371 (c)(1),
(2), (4) Date: May 2, 2012

(87) PCT Pub. No.: WO2011/055979
PCT Pub. Date: May 12, 2011

(65) Prior Publication Data
US 2012/0308676 A1     Dec. 6, 2012

(30) Foreign Application Priority Data

Nov. 3, 2009  (KR) .................. 10-2009-0105438
Nov. 3, 2009  (KR) .................. 10-2009-0105439
Nov. 3, 2010  (KR) .................. 10-2010-0108831
Nov. 3, 2010  (KR) .................. 10-2010-0108832

(51) Int. Cl.
*A61K 36/47* (2006.01)
*A61K 36/83* (2006.01)

(52) U.S. Cl.
CPC .................. *A61K 36/47* (2013.01); *A61K 36/83* (2013.01)

(58) Field of Classification Search
None
See application file for complete search history.

(56) References Cited

FOREIGN PATENT DOCUMENTS

| EP | 0515561 B1 | 8/1996 |
|---|---|---|
| JP | 10-287617 A1 | 10/1998 |
| WO | WO 2008/093902 A1 | 8/2008 |
| WO | WO 2008/133851 A1 | 11/2008 |
| WO | WO 2009/052600 A2 | 4/2009 |

OTHER PUBLICATIONS

Griffiths (Rev. Med. Virol. (2006), vol. 16, pp. 135-138).*
Pauwels (Antiviral Research (2006), vol. 71, pp. 77-89).*
Cho et al. "Cell Scattering Activity of Natural Plant Extracts," *Korean Journal of Pharmacognosy*, 35(1): 62-79 (2004).

* cited by examiner

*Primary Examiner* — Susan Hoffman
(74) *Attorney, Agent, or Firm* — Klarquist Sparkman, LLP

(57) ABSTRACT

The present invention relates to an antiviral composition containing an *Aleurites fordii* or *Daphne kiusiana* extract or a fraction thereof as an active ingredient. In detail, extracts of *Aleurites fordii* or *Daphne kiusiana* or fractions thereof can induce the secretion of an immune-related cytokine, interferon-$\gamma$ (IFN-$\gamma$) in natural killer (NK) cells, and thus exhibit potent antiviral activity and superior effects for viral diseases, and therefore can be effectively used in an antiviral composition.

6 Claims, 11 Drawing Sheets

Fig. 3
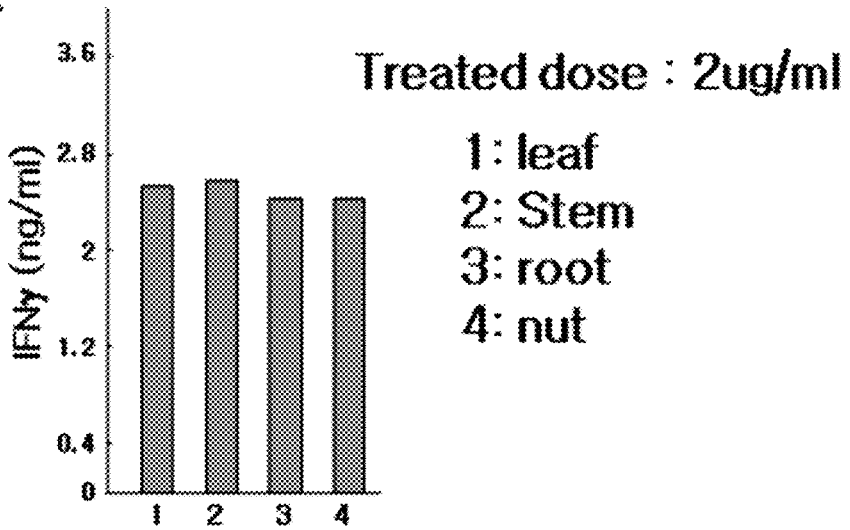
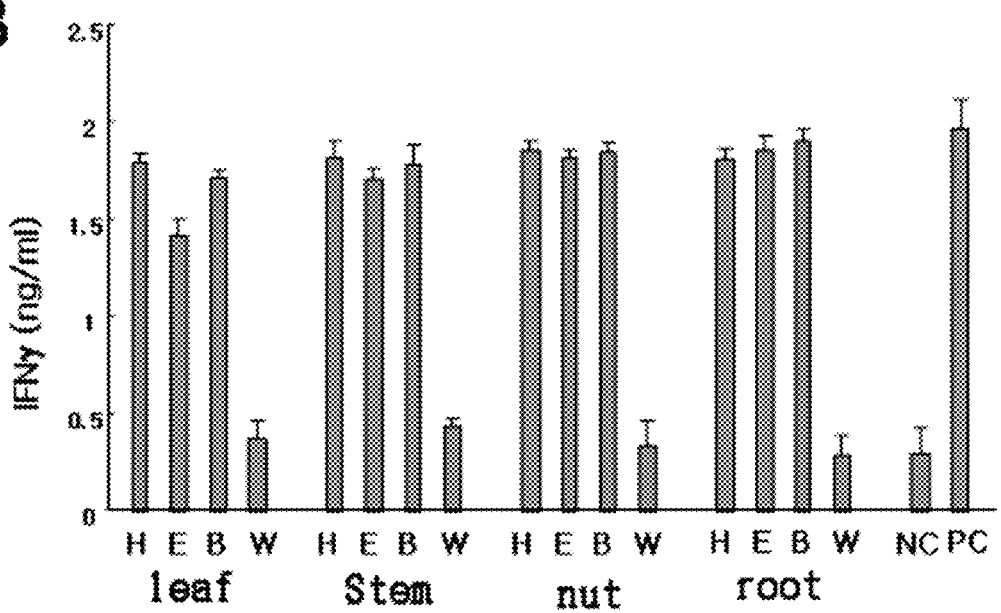

ANTIVIRAL COMPOSITION CONTAINING AN *ALEURITES FORDII* OR *DAPHNE KIUSIANA* EXTRACT OR A FRACTION THEREOF AS AN ACTIVE INGREDIENT

CROSS REFERENCE TO RELATED APLICATIONS

This is the U.S. National Stage of International Application No. PCT/KR2010/007724 filed on Nov. 3, 2010, which in turn claims the benefit of Korean Patent Application No. 10-2009-0105438 filed on Nov. 3, 2009, Korean Patent No. 10-2009-0105439 filed on Nov. 3, 2009, Korean Patent Application No. 10-2010-0108831 filed on Nov. 3, 2010, and Korean Patent Application No. 10-2010-0108832 filed on Nov. 3, 2010.

BACKGROUND OF THE INVENTION

1. Field of the Invention

The present disclosure relates to antiviral compositions containing an *Aleurites fordii* or *Daphne kiusiana* extract or a fraction thereof as an active ingredient.

2. Description of the Related Art

Many infectious diseases in humans are caused by viruses and viruses can lead to a variety of serious diseases such as rabies, smallpox, myelitis, hepatitis, yellow fever, immune deficiency, encephalitis, and AIDS. These viral infectious diseases, for example, flu, measles, mumps, and chickenpox, are highly contagious, and result in not only acute symptoms but also respiratory or digestive disorders. Some viruses such as measles viruses and cytomegaloviruses can cause birth defects and other viruses which are known as oncogenic viruses can cause tumors and cancers in humans. Therefore, research on antiviral drugs has long been carried out robustly until now. Antiviral drugs weaken or dissipate actions of viruses that attacked human body and include Oseltamivir (Tamiflu), Zanamivir (Relenza), Interferon, immunoglobulin preparations, etc. However, there are some problems with the continuous use of conventional antiviral drugs which have been used for the prevention and treatment of viral infectious diseases due to viral resistance and side effects of mutant viruses against these drugs. Therefore, development of new, natural products-derived antiviral drugs which are capable of solving the problems of conventional antiviral drugs is required, and particularly, development of non-toxic natural materials to be suitable for medicines and food additives is required.

Interferon-γ (IFN-γ) is a natural protein produced by activated T-cells and natural killer (NK) cells in the immune system in response to the invasion of exogenous substances such as viruses, parasites, and tumor cells. IFN-γ is a dimeric cytokine released by T-helper 1 (Th1) cells, cytotoxic T (Tc) cells, dendritic cells, or NK cells in response to the presence of double-stranded RNA, an important indicator of viral infection, and the member of the type II class of interferons. IFN-γ has a strong macrophage-activating action to be originally called macrophage-activating factor. According to current research, IFN-γ induces transcriptional changes in about 30 genes, producing a variety of immune and cellular responses: increase in antigen presentation of macrophages, increase in lysosome activity of macrophages and activation of lysosome in macrophages; suppression of Th2 cell activity; increase in expression of class I MHC molecules in normal cells; increase in leukocyte migration; and increase in NK cell activity. IFN-γ inhibits viral replication, activates NK cells, increases antigen presentation to lymphocytes, and increases resistance to viral infection in host cells, helping immune responses. When antigen is presented to T and B cells to be matched, these cells differentiate and remove exogenous substances in a strategic and specific way. In this respect, antigen presentation is a very important mechanism in the immune response.

NK cells are known to involve in innate and acquired immune responses. NK cells mediate their effector functions through cytotoxicity and cytokine production and function as cytotoxic cells mediated by receptors and ligands for target cells. NK specific receptors for cytotoxicity include NKp46 (Sivori, S. et al., *J Exp Med*, 186: 1129-1136, 1997), NKp30 (Pende, D. et al., *J Exp Med*, 190: 1505-1516, 1999), and NKp44 (Cantoni, C. et al., *J Exp Med*, 189: 787-796, 1999) which are called natural cytotoxic receptors (NCRs). Known ligands for NCRs include hemagglutinin (HA) of influenza virus (IV), hemagglutinin-neuraminidase (HN) of Sendai virus (SV) (Amon, T. I. et al., *Eur J Immunol*, 31: 2680-2689, 2001), and membrane-associated heparin sulfate proteoglycans (Bloushtain, N. et al., *J Immunol*, 173: 2392-2401, 2004). NK cells also play an important role in helping development of acquired immune response through secretion of cytokines such as IFN-γ(Stetson, D. B. et al., *J Exp Med*, 198: 1069-1076, 2003), and IFN-γ was reported to have an antiviral activity in murine cytomegalovirus infection. NK cells are involved in both direct innate defense and formation of acquired immune response. NK cells inhibited tumor development and microorganism infection in several mouse models. Particularly, NK cells kill virus-infected cells directly in the initial phase of mouse cytomegalovirus (MCMV) infection and produce IFN-γ, playing a role as a regulator. The major pathway of IFN-γ production in NK cells depends on the activation of protein kinase Cθ (PKCθ). Researchers led by Tassi reported that engagement of NK cell receptors which signal through immunoreceptor tyrosine-based activation motif (ITAMs) results in prompt activation of PKCθ. Analyses of NK cells from PKCθ-deficient mice indicated that PKCθ is a required factor for ITAM-mediated IFN-γ secretion (Tassi, I. et al., *Blood*, 112: 4109-4116, 2008).

Phospholipase Cγ (PLCγ) is a very intrinsic base factor in IFN-γ secretion. The basal level of IFN-γ production was significantly reduced in PLCγ2-deficient NK cells, and, in contrast to wild type cells, stimulation with anti-NK1.1 resulted in no augmentation of IFN-γ release (Caraux, A. et al., *Blood*, 107: 994-1002, 2006). The PLCγ2-deficient NK cells were severely impaired in their ability to produce either IFN-γ or granulocyte-macrophage colony stimulating factor (GM-CSF), and PLCγ2 plays a critical role in the NKG2D as well as NK1.1-mediated cytokine production (Regunathan, J. et al., *J Immunol*, 177: 5365-5376, 2006). In mouse, these include the γ-chain of Fc receptor (FcRs) and engagement of this receptor results in tyrosine phosphorylation of the associated adaptors' ITAMs, which recruit spleen tyrosine kinase (Syk). This kinase activates multiple downstream signaling mediators, including linker for activation of T cells, SH2 domain-containing leukocyte protein of 76 kDa, PLC, PI3K, and the Erk kinases. Collectively, these signaling mediators trigger gene transcription and the cellular programs for exocytosis of lytic granules that allow NK cells to lyse target cells and produce proinflammatory chemokines and cytokines, particularly IFN-γ (Tassi, I. et al., *J Immunol*, 175: 749-754, 2005). As described above, since IFN-γ exerts antiviral, antiproliferative, and immune regulatory effects, it has been used for the treatment of hepatitis, various viral infectious diseases, and cancer.

Meanwhile, most viruses have immune evasion strategies to protect themselves against host IFN responses. Particularly, various mechanisms about inhibition of IFN-γ signaling by viruses have been reported. For example, an Epstein-barr virus was known to inhibit expression of the IFN-γ receptor gene and prevent antiviral IFN responses (Morrison, T. E., et al., *Immunity* 15:787-799, 2001), a human tumor-inducing herpesvirus was known to inhibit the IFN-γ receptor 1 (Li, Q., *J Virol* 81, 2117-2127, 2007). Therefore, development of a substance to promote the secretion and the activity of IFN and thus, enhance antiviral activity and immune activity is required.

Tung tree (*Aleurites fordii*) is a deciduous tree in the Euphorbiaceae family, Geraniales, Magnoliopsida. Its scientific name is *Aleurites fordii* and it is also commonly called "tung oil tree". It grows in China and also in the southern coast of South Korea. Trees grow up to approximately 7.5 to 10 m tall, the bark is grayish brown, lenticellate, and thick branches are wide spreading in all directions. Leaves are alternate, heart-shaped or round and reddish white flowers bloom in May. The fruit is a capsule, ripens in September, is round, and contains three seeds per capsule. In the south, *Aleurites fordii* is planted as a shade tree or garden tree. From seeds, oil is collected and the oil is called "tung oil." In the Orient, tung oil was traditionally used for lightening, but it also has important modern industrial uses.

The fruit of *Aleurites fordii* has efficacies in promoting spitting phlegm due to wind, reducing swelling and detoxifying, and inducing urination and defecation, and was used for the treatment of pharyngitis induced by wind phlegm (laryngeal tuberculosis, syphilis of larynx, etc.), scabies, erysipelas, scalding injuries, impetigo, dyspepsia, and fecal and urinary disorder in the Oriental traditional medicine. Roots have efficacies in digesting foods, removing water well, removing phlegm, and removing a parasite, and were used for the treatment of feels heavy due to retention of digested food, edema, abdominal distention, wheezing asthma, scrofula, and ascariasis. Leaves are efficacies in treating carbuncle, cellulites, and swelling an injury, and detoxifying, and were used for the treatment of furuncle, erysipelas, boils in the shinbone, frostbite, scabies, and dysentery (Bosup Chung, Minkyo Shin, Illustrated unabridged dictionary of native herbal drugs, Youngrimsa, Seoul, Korea. pp. 741-742, 1998).

Research on chemical constituents of *Aleurites fordii* showed that *Aleurites fordii* contains diterpenoid esters, sterols, tannins, oil, coumarin, and coumarolignan-based compounds (Ishikura, N. et al., *I. Botanical Magazine*, 88: 41-45, 1975; Nonaka, G. et al., *Chem. Pharm. Bull.* 38: 861-865, 1990; Fozdar, B. I. et al., *Phytochemistry* 28, 2459-2461, 1989; Hiroto, M. et al., *Agricultural and Biological Chemistry* 43, 2523-2529, 1979; Okuda, T. et al., *Phytochemistry* 14, 509-515, 1975). Research on bioactivity of *Aleurites fordii* revealed a human polymorphonuclear leukocyte activating factor, a human neutrophil-activating factor, etc., and extracts of *Aleurites fordii* and diterpene esters were reported to induce Epstein-Barr virus activation. 12-O-hexadecanoyl-16-hydroxyphorbol 13-acetate of *Aleurites fordii* was reported to have the efficacy in increasing human T-lymphotrophic virus type I (HTLV-I)-induced colony formation of lymphocytes. 12-O-Palmitoyl-16-hydroxyphorbol 13-acetate and 12-O-palmitoyl-4-deoxy-4β-16-hydroxyphorbol 13-acetate of *Aleurites fordii* was known to have similar toxicity to fish with rotenone (Hiroto, M. et al., *Agricultural and Biological Chemistry* 43, 2523-2529, 1979; Okuda, T. et al., *Phytochemistry* 14, 2513-2514, 1975; Shichijo, S. et al, *Journal of Clinical Laboratory Immunology* 27, 183-189, 1988; Matsuda, S. et al., *International Journal of Cancer* 38, 859-865, 1986; Shichijo, S. et al., *Arerugi* 34, 190-197, 1985; Ito, Y. et al., *Cancer Letters* 18, 87-95, 1983).

*Daphne kiusiana* is an evergreen broad-leaved shrub in the Thymelaeaceae family, Myrtales, Magnoliopsida. Its scientific name is *Daphne kiusiana* and it is also called "white daphne." It is native to South Korea, and grows mainly at an altitude of 50 to 1,300 m of the foot of mountains by seas in Geojedo in Gyeongsangnam-do, Heuksando in Jeollanam-do, and Jeju Island. It is about 1 m tall. Leaves are alternate, oval or oblanceolate, about 3 to 8 cm long, about 1.2 to 3.5 cm wide, even-edged, glossy, acute at the base connected to short petioles. Flowers are dioecious, bloom white from February to April, on the top of branches in clusters, and have a strong scent. The bract is wide lanceolate, pedicels are short with grey pubescence, and calyx also has pubescence and is divided into 4 sepals. The fruit is a berry, like an egg-shaped ball, about 8 mm long, and ripen into scarlet in May, June. Stems are straight up, royal blue, multi-branched to form a spreading tree form.

Flowers of *Daphne kiusiana* have been used for the treatment of laryngopharyngitis, toothache, rheumatic pains, abdominal distention, and early mammary cancer, roots have been used for the treatment of a sore throat, and leaves have been used for the treatment of a wound, a gout, and chronic dermatitis in the Oriental traditional medicine. However, the biological activity has not been clearly known yet (Bosup Chung, Minkyo Shin, Illustrated unabridged dictionary of native herbal drugs, Youngrimsa, Seoul, Korea. pp. 741-742, 1998). Research on chemical constituents of *Daphne kiusiana* reported that *Daphne kiusiana* contains anthocyanin-based and coumarin-based compounds (Ishikura, N, I. *Botanical Magazine*, 88: 41-45, 1975; Nakabayashi, T, *Yakugaku Zasshi*, 74: 192-193, 1954).

However, there has been no report about anti-viral activity and immune-activating action of *Aleurites fordii* or *Daphne kiusiana*.

Thus, the present inventors have performed research to search for antiviral materials being capable of solving problems of conventional antiviral drugs from plant-derived natural extracts, and found that extracts or fractions of leaves, stems, and fruits of *Aleurites fordii*, and extracts or fractions of leaves, stems, flowers, and roots of *Daphne kiusiana*, increased interferon-γ (IFN-γ) secretion in natural killer (NK) cells remarkably, and had antiviral effects, thereby leading to completion of the present invention.

SUMMARY OF THE INVENTION

One object of the present invention is to provide an antiviral composition containing an *Aleurites fordii* or *Daphne kiusiana* extract or a fraction thereof as an active ingredient.

Another object of the present invention is to provide a method for alleviating or treating viral diseases, the method comprising administering a composition containing a pharmaceutically effective amount of the *Aleurites fordii* or *Daphne kiusiana* extract or the fraction thereof as an active ingredient to an individual having a viral disease.

Still another object of the present invention is to provide a method for preventing viral diseases, the method comprising administering a composition containing a pharmaceutically effective amount of the *Aleurites fordii* or *Daphne kiusiana* extract or the fraction thereof as an active ingredient to an individual.

In order to achieve the objects, the present invention provides a pharmaceutical composition for preventing or treating viral diseases, the pharmaceutical composition comprising the *Aleurites fordii* or *Daphne kiusiana* extract as an active ingredient.

The present invention also provides a pharmaceutical composition for preventing or treating viral diseases, the pharmaceutical composition comprising an organic solvent fraction as an active ingredient, wherein the organic solvent fraction is prepared by further extracting the *Aleurites fordii* or *Daphne kiusiana* extract with an organic solvent.

Furthermore, the present invention provides a healthy food for preventing or alleviating viral diseases, the health food comprising the *Aleurites fordii* or *Daphne kiusiana* extract or the fraction thereof as an active ingredient.

The present invention also provides a feed additive for preventing or alleviating viral diseases, the feed additive comprising the *Aleurites fordii* or *Daphne kiusiana* extract or the fraction thereof as an active ingredient.

Furthermore, the present invention provides a method for alleviating or treating viral diseases, the method comprising administering a pharmaceutical composition to an individual having a viral disease, wherein the pharmaceutical composition comprises a pharmaceutically effective amount of the *Aleurites fordii* or *Daphne kiusiana* extract or the fraction thereof as an active ingredient.

The present invention also provides a method for preventing viral diseases, the method comprising administering a composition containing a pharmaceutically effective amount of the *Aleurites fordii* or *Daphne kiusiana* extract or the fraction thereof as an active ingredient to an individual.

Furthermore, the present invention provides a use of the *Aleurites fordii* or *Daphne kiusiana* extract or the fraction thereof for the preparation of a pharmaceutical composition for preventing or treating viral diseases.

The present invention also provides a use of the *Aleurites fordii* or *Daphne kiusiana* extract or the fraction thereof for the preparation of a healthy food for preventing or alleviating viral diseases.

Furthermore, the present invention provides a use of the *Aleurites fordii* or *Daphne kiusiana* extract or the fraction thereof for the preparation of a feed additive for preventing or alleviating viral diseases.

Extracts of *Aleurites fordii* or *Daphne kiusiana*, or fractions thereof of the present invention can induce the secretion of an immune-related cytokine IFN-γ in NK cells, and thus exhibit potent antiviral activity and superior effects for viral diseases, and therefore, can be effectively used for antiviral compositions as an active ingredient.

BRIEF DESCRIPTION OF THE DRAWINGS

The above and other objects, features and other advantages of the present invention will be more clearly understood from the following detailed description taken in conjunction with the accompanying drawings, in which:

FIG. 3 is a graph showing the result of analyzing IFN-γ secretion in NK92 cells treated with each methanol extract of leaves, stems, flowers, and roots of *Daphne kiusiana*, n-hexane fraction, ethylacetate fraction, butanol fraction, or water fraction, fractionated from the methanol extract:
  A: methanol extract of *Daphne kiusiana*; and
  B: organic solvent fraction of methanol extract of *Daphne kiusiana*:
  M: methanol extract of *Daphne kiusiana*;
  H: n-hexane fraction of *Daphne kiusiana*;
  E: ethylacetate fraction of *Daphne kiusiana*;
  B: butanol fraction of *Daphne kiusiana*;
  W: water fraction of *Daphne kiusiana*;
  NC: negative control; and
  PC: positive control.

DESCRIPTION OF THE PREFERRED EMBODIMENTS

Figure 1:
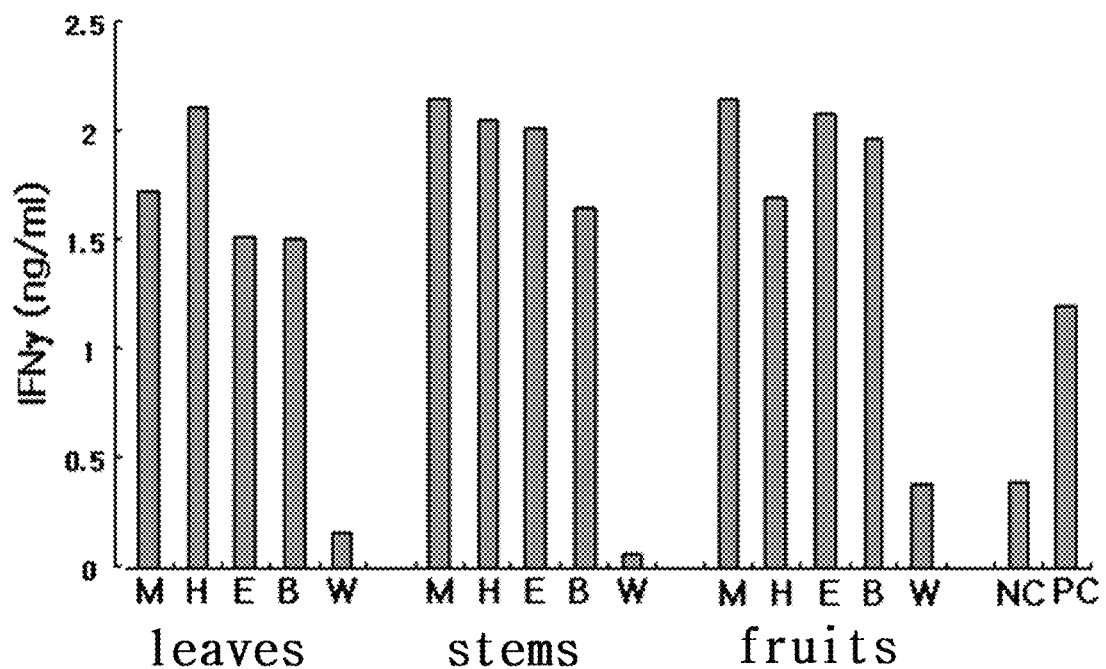
FIG. 1 is a graph showing the result of analyzing IFN-γ secretion in NK92 cells treated with each methanol extract of leaves, stems, and fruits of *Aleurites fordii*, n-hexane fraction, ethylacetate fraction, butanol fraction, or water fraction, fractionated from the methanol extract:
  M: methanol extract of *Aleurites fordii*;
  H: n-hexane fraction of *Aleurites fordii*;
  E: ethylacetate fraction of *Aleurites fordii*;
  B: butanol fraction of *Aleurites fordii*;
  W: water fraction of *Aleurites fordii*;
  NC: negative control; and
  PC: positive control.

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, terms used in the present invention will be described.

The term "extract" used in the present specification has the meaning of a crude extract which is commonly used in the art, but, in a broad sense, the term includes also the following fraction.

The term "fraction" used in the present specification refers to an activity fraction, which is obtained by fractionating an activity of interest in the present invention with a solvent different from a solvent used in extraction.

The term "prevention" used in the present invention refers to all behavior inhibiting viral diseases or delaying progress of viral diseases by the administration of a composition of the present invention.

The terms "treatment" and "alleviation" used in the present invention refer to all behavior making symptoms of viral diseases better or changing them more favorable by the administration of the composition of the present invention.

The term "administration" used in the present invention refers to providing the composition of the present invention for an individual in an arbitrary suitable way.

The term "individual" used in the present invention refers to all animals having a disease of which symptoms of viral diseases can be made better by administering the composition of the present invention, such as humans, monkeys, dogs, goats, pigs, rats, etc.

The term "feed" used in the present specification refers to a substance offering organic or inorganic nutrients required to maintain livestock's life and produce milk, meats, eggs, furs, etc.

Hereinafter, the present invention will be described in detail.

The present invention provides a pharmaceutical composition for preventing or treating viral diseases containing an *Aleurites fordii* or *Daphne kiusiana* extract as an active ingredient.

The *Aleurites fordii* or *Daphne kiusiana* extract, or fractions thereof may be obtained by various extraction methods that are well-known in the arts.

The *Aleurites fordii* or *Daphne kiusiana* extract may be prepared by, but not limited to, a preparation method comprising the following steps of:

(1) adding an extraction solvent to *Aleurites fordii* or *Daphne kiusiana* and extracting an *Aleurites fordii* or *Daphne kiusiana* extract;

(2) cooling and filtering the extract in step (1); and (3) concentrating the filtered extract in step (2) under reduced pressure and drying the concentrated extract.

In the above method, *Aleurites fordii* or *Daphne kiusiana* may be any *Aleurites fordii* or *Daphne kiusiana* without limitation, including cultivated or purchased *Aleurites fordii* or *Daphne kiusiana*. Each of dried leaves, stems, or fruits of *Aleurites fordii* may be used, and each of dried leaves, stems, flowers, or roots of *Daphne kiusiana* may be used.

The extraction solvent may be any extraction solvents that are conventionally used in the arts, and preferably, water, an alcohol, or a mixture thereof. The alcohol may be a lower alcohol of $C_1$ to $C_2$. The lower alcohol may be ethanol or methanol. Extraction method may be, but not limited to, shaking extraction, reflux extraction, supercritical extraction, or subcritical extraction. The amount of the extraction solvent added to *Aleurites fordii* or *Daphne kiusiana* may be from about 2-fold to about 20-fold of the amount of dried *Aleurites fordii* or *Daphne kiusiana*. Extraction temperature may be, but not limited to, from about 20 to about 50° C. Extraction time may be, but not limited to, from about 10 to about 48 hr, preferably 24 hr. Extraction may be repeated three to five times, preferably three times, but it is not limited to such.

In the above method, concentration under reduced pressure in step (3) may use, but not limited to, a vacuum reduced pressure concentrator or vacuum rotary evaporator. Drying may be, but not limited to, reduced pressure drying, vacuum drying, boiling drying, spray drying, or freeze drying.

The fraction of the *Aleurites fordii* or *Daphne kiusiana* extract may be prepared by, but not limited to, a preparation method comprising adding an organic solvent additionally to the *Aleurites fordii* or *Daphne kiusiana* extract and preparing an organic solvent fraction.

In the method, the organic solvent may be any extraction solvents that are conventionally used in the arts, and may be anhydrous or hydrous lower alcohol of $C_1$ to $C_4$ (methanol, ethanol, propanol, butanol, n-propanol, iso-propanol or n-butanol, etc.), a mixed solvent of the lower alcohol and water, acetone, ethylacetate, chloroform, 1,3-butylene glycol, hexane, diethyl ether, or butyl acetate, etc. Preferably, the organic solvent may be, but not limited to, hexane, ethylacetate, or butanol.

Fractions of each organic solvent layer obtained by adding hexane, ethylacetate, butanol, and water in terms of increasing polarity (lowest to highest) to the *Aleurites fordii* or *Daphne kiusiana* extract may be preferred and fractions may be fractionated by using a separatory funnel, but, it is not limited to such. Specifically, the *Aleurites fordii* or *Daphne kiusiana* extract may be suspended in distilled water, and hexane may be added thereto, then a hexane layer may be separated; ethylacetate may be added again to the remaining water layer, and an ethylacetate layer may be separated; and butanol may be added again to the remaining water layer and then, a butanol layer may be separated. All fractions of each organic solvent layer can be used.

The *Aleurites fordii* or *Daphne kiusiana* extract, or fractions thereof, may exert antiviral activity through, but not limited to, induction of interferon-γ (IFN-γ) secretion in natural killer (NK) cells.

The viral disease may be, but not limited to, a disease infected with one or more viruses selected from the group consisting of Swine Influenza virus (SIV), influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV) and hepatitis virus.

The composition of the present invention may further contain one or more active ingredients having a same or similar function in addition to the above ingredient.

The *Aleurites fordii* or *Daphne kiusiana* extract, or fractions thereof, may be contained, but not limited to, from about 0.1 to about 50 parts by weight, based on the total weight of the composition of the present invention.

The composition of the present invention may comprise pharmaceutically acceptable carriers in addition to the above described active ingredients. The pharmaceutically acceptable carrier comprised in the composition of the present invention may be any carriers that are conventionally used in preparations. Examples of the pharmaceutically acceptable carrier may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, mineral oil, etc. The composition of the present invention may further comprise lubricants, wetting agents, sweeteners, aromatics, emulsifiers, suspensions, preservatives, etc. in addition to the above ingredients. Suitable pharmaceutically acceptable carriers and preparations are described in *Remington's Pharmaceutical Sciences* (19th ed., 1995) in detail.

The suitable administration dose of the composition of the present invention may be variously prescribed depending on factors, such as preparation method, administration method, age, body weight, gender, health condition of patient, diet, administration time, administration route, excretion rate, and response sensitivity, etc. Oral administration dose of the composition of the present invention may be, but not limited to, from about 0.0001 to about 100 mg/kg body weight per day.

The composition of the present invention may be administered orally or parenterally. For parenteral administration, intravenous injection, subcutaneous injection, intramuscular injection, intraperitoneal injection, dermal administration, etc. may be selected. The administration route of the composition of the present invention may be determined depending on the kind of disease applied.

The composition of the present invention may be prepared by using pharmaceutically acceptable carriers and/or excipients into a unit dosage form or by being captured in a multi-dose container, according to methods that would be accomplished by those skilled in the art. The formulation may be oil or a solution in aqueous medium, suspension or emulsion, or extracts, powders, granules, tablets, or capsules, and may further comprise dispersants or stabilizers.

Figure 4:
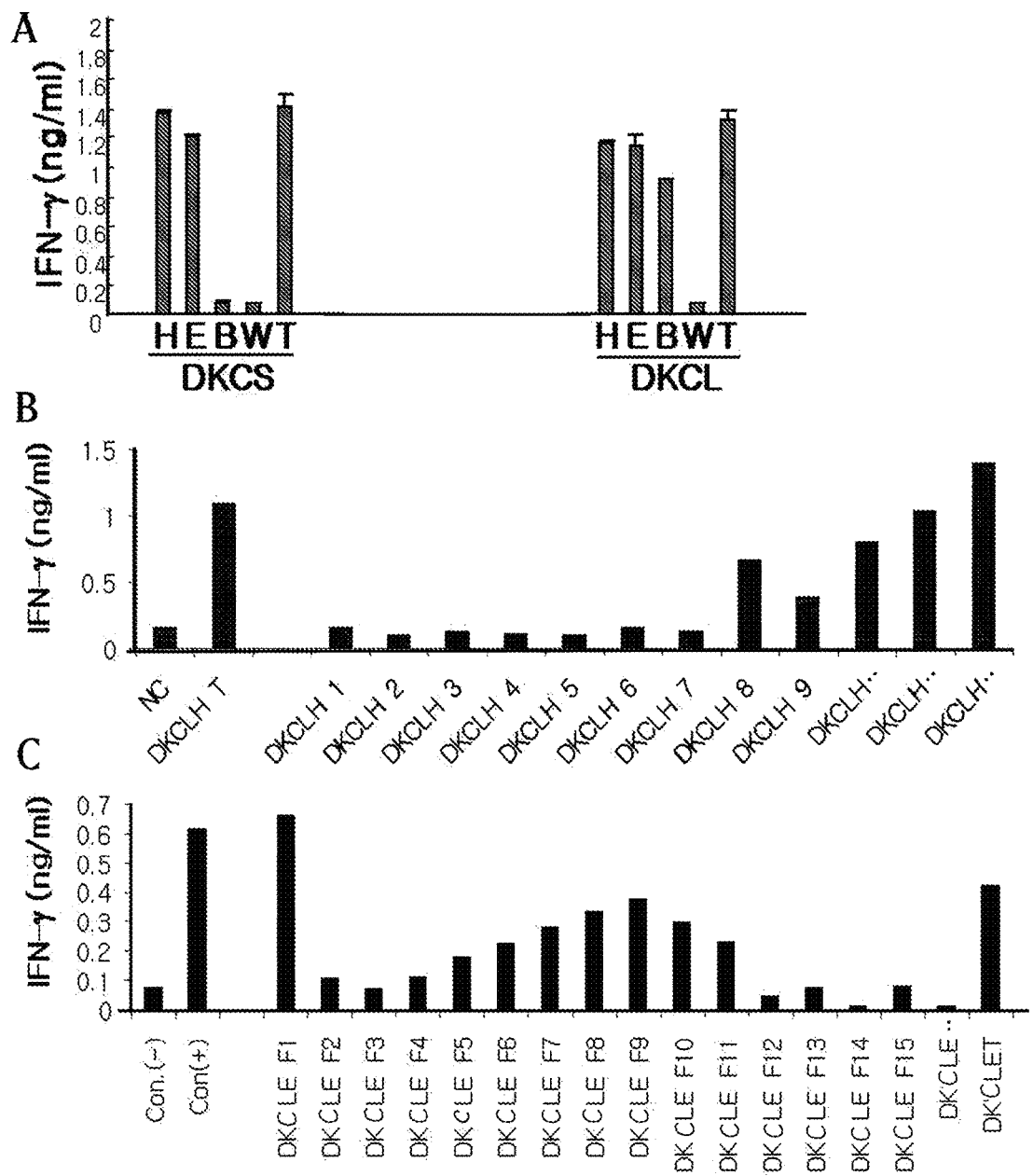
FIG. 4 is graphs showing the result of analyzing IFN-γ secretion in NK92 cells treated with each fraction fractionated from each extract of leaves, stems, flowers, and roots of *Daphne kiusiana*:
  A: organic solvent fraction of methanol extract of *Daphne kiusiana* (DKCS: stems of cultivated *Daphne kiusiana* sample; and DKCL: leaves of cultivated *Daphne kiusiana* sample);
  B: n-hexane fraction of leaves of cultivated *Daphne kiusiana* sample; and
  C: ethylacetate fraction of leaves of cultivated *Daphne kiusiana* sample leaves.
Figure 5:
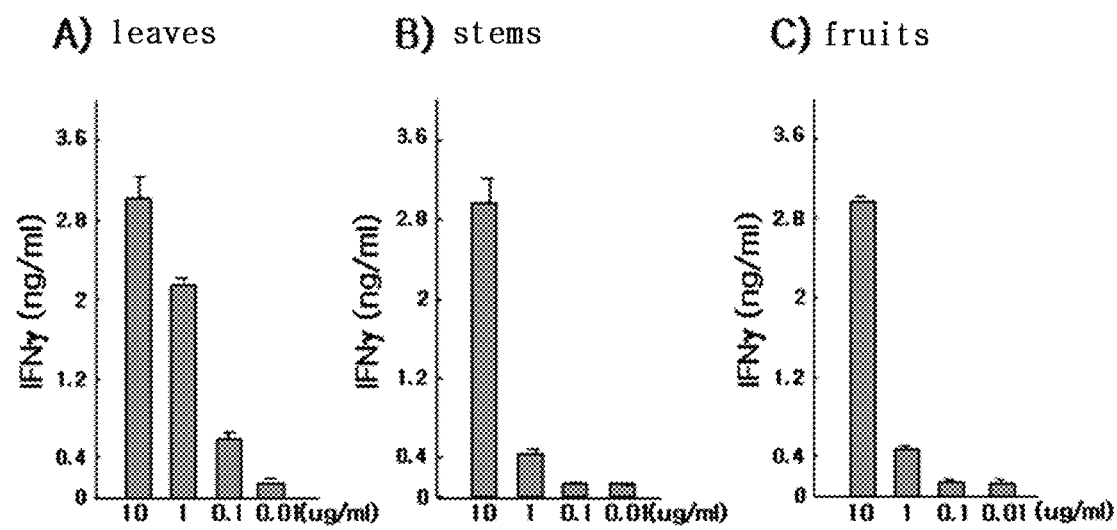
FIG. 5 is graphs showing the result of analyzing IFN-γ secretion in NK92 cells treated with different concentrations of each methanol extract of leaves, stems, and fruits of *Aleurites fordii*.
Figure 6:
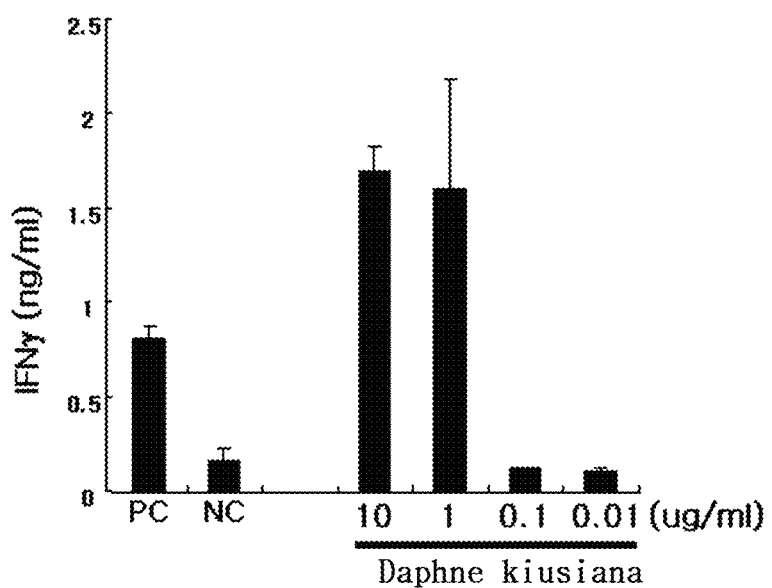
FIG. 6 is a graph showing the result of measuring the minimum active concentration of the ability to produce IFN-γ of the *Daphne kiusiana* extract.
Figure 7:
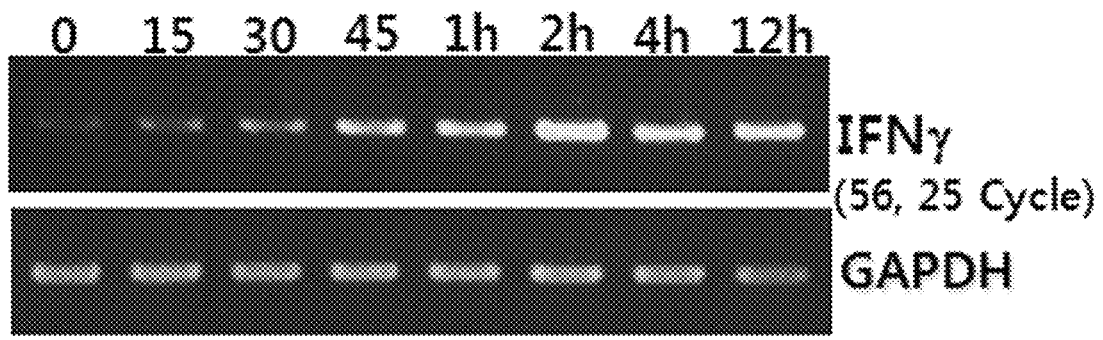
FIG. 7 is a diagram showing IFN-γ mRNA expression measured at different times in NK92 cells treated with the *Aleurites fordii* extract through RT-PCR.
Figure 8:
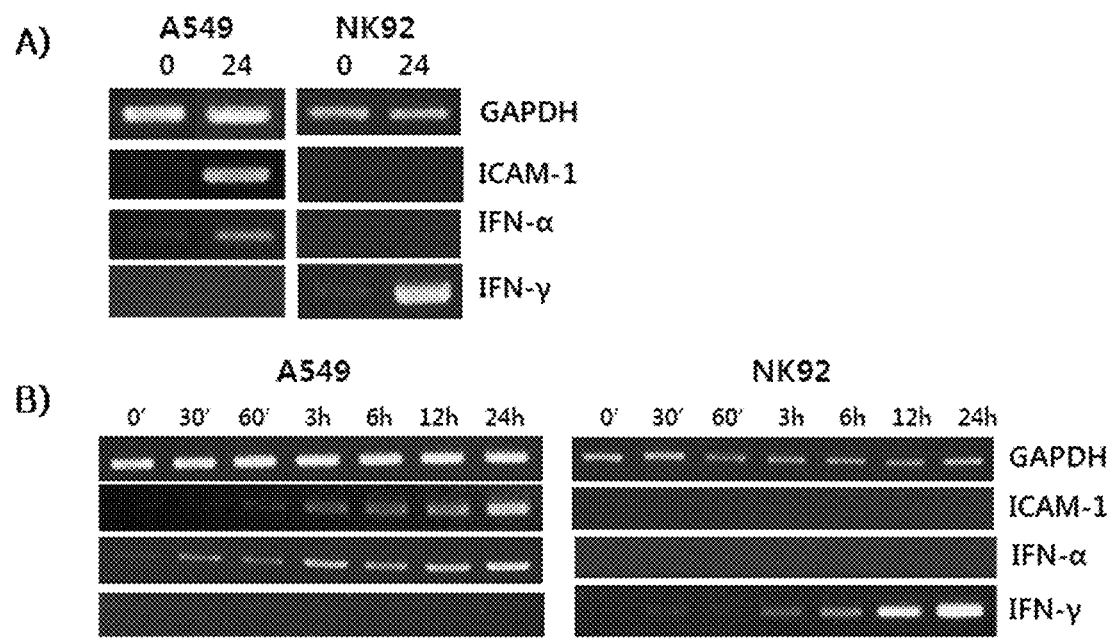
FIG. 8 is a diagram showing IFN-α and -γ mRNAs expression measured at different times in NK92 cells treated with the *Daphne kiusiana* extract through RT-PCR.
Figure 9:
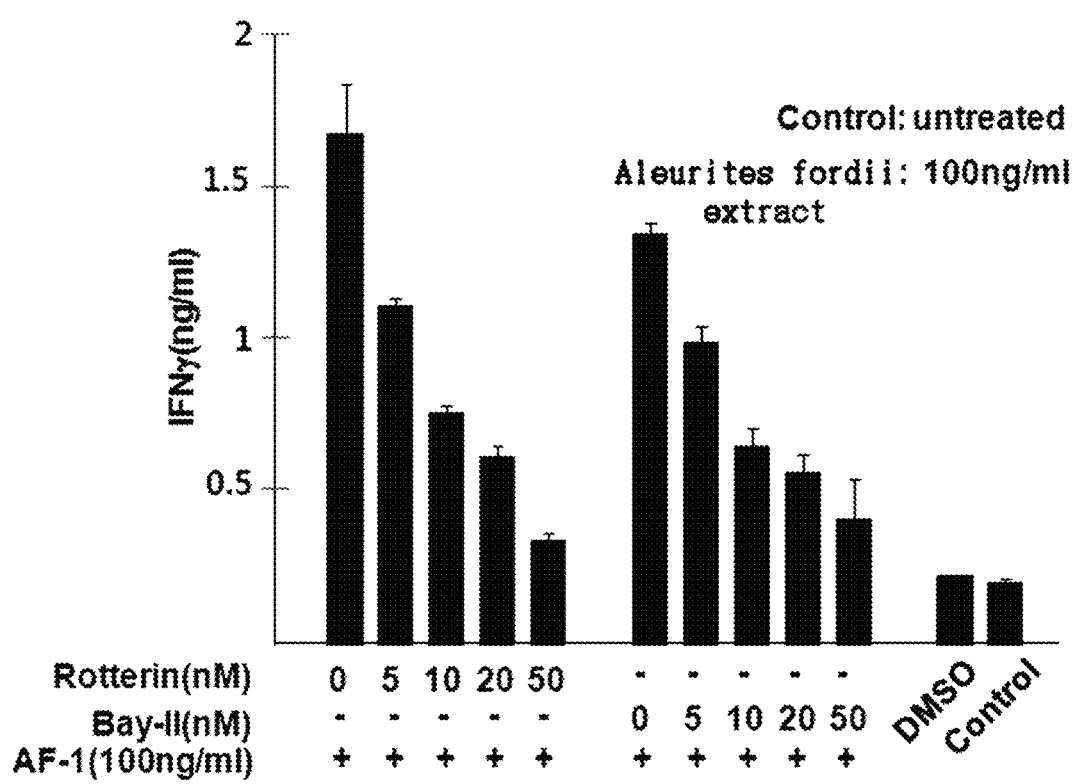
FIG. 9 is a diagram showing the *Aleurites fordii* extract-induced change in IFN-γ production following Bay-II (NF-κB activity inhibitor) or Rotterin (PKC activity inhibitor) treatment;
  AF-1: *Aleurites fordii* extract.
Figure 10:
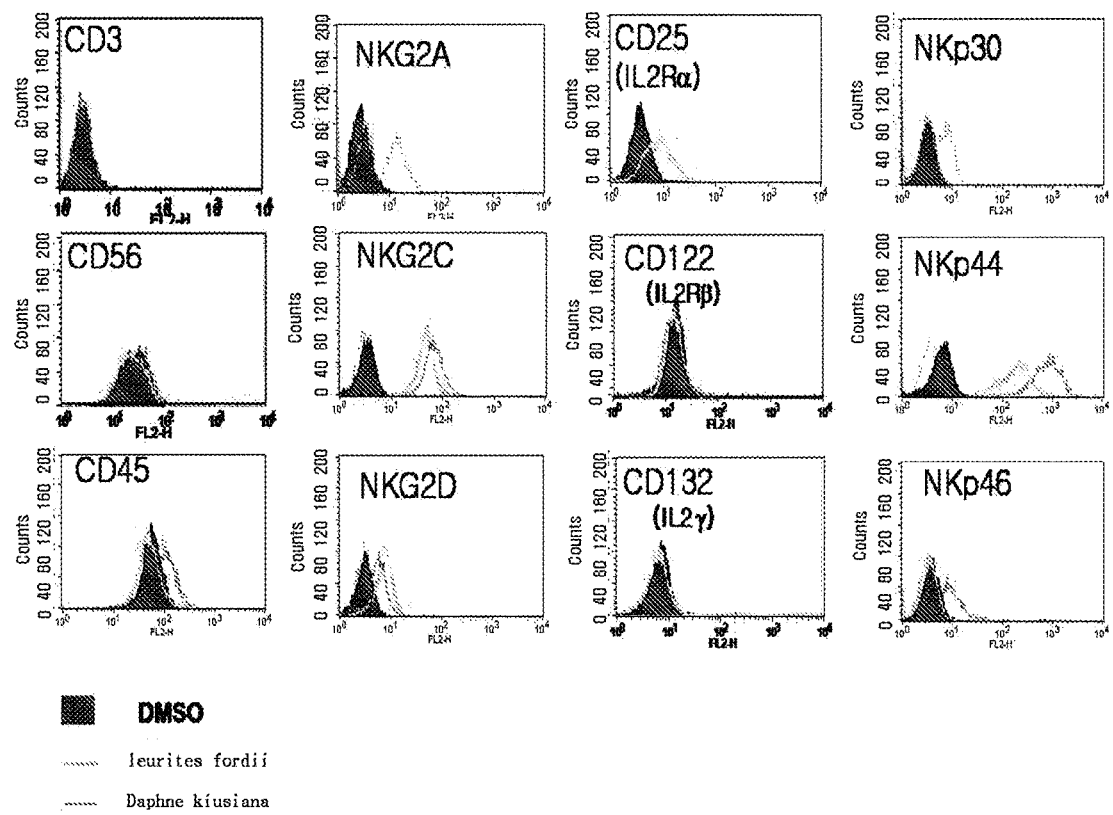
FIG. 10 is diagrams showing the result of analyzing changes in expressions of cell surface substances involving the activity of NK92 cells treated with the *Aleurites fordii* extract or *Daphne kiusiana* extract through FACS.
Figure 11:
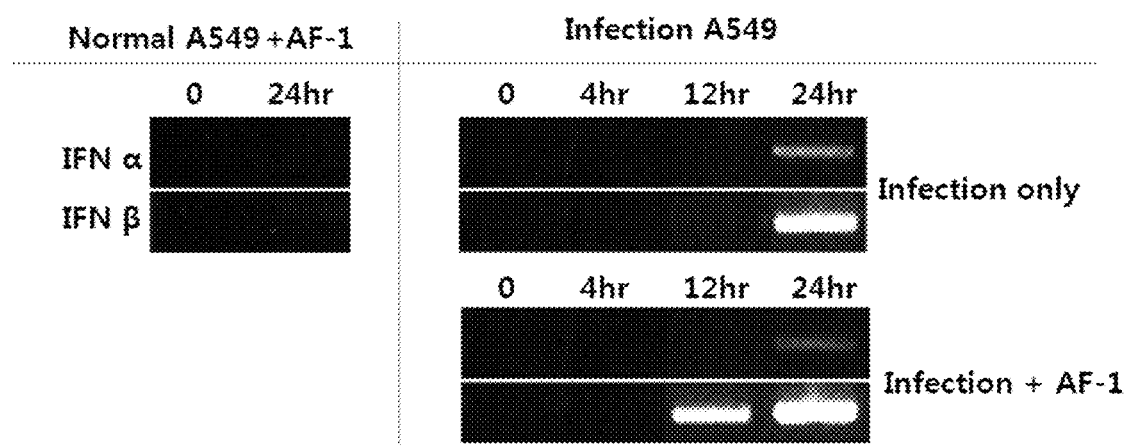
FIG. 11 is a diagram showing IFN-α and IFN-β mRNAs expression in the influenza virus-infected lung epithelial A549 cells by the *Aleurites fordii* extract treatment through RT-PCR;
  AF-1: *Aleurites fordii* extract.

To investigate the antiviral activity of extracts of *Aleurites fordii* or *Daphne kiusiana* or fractions thereof, the present inventors examined the ability to induce interferon-γ (IFN-γ) secretion of extracts of *Aleurites fordii* or *Daphne kiusiana* or fractions thereof through enzyme-linked immunosorbent assay (ELISA). Consequently, extracts of *Aleurites fordii* leaves, stems, or fruits, or fractions thereof (n-hexane fraction, ethylacetate fraction, or butanol fraction) increased significantly the secretion of IFN-γ in NK cells (Table 1, FIG. 1, and FIG. 2), and the secretion of IFN-γ increased in a dose-dependent manner with increasing concentrations of *Aleurites fordii* extracts (FIG. 5). In addition, each extract of *Daphne kiusiana* leaves, stems, flowers, or roots, or fractions thereof (n-hexane fraction, ethylacetate fraction, or butanol fraction) increased significantly the secretion of IFN-γ in NK cells (Table 2, FIG. 3, and FIG. 4), and the secretion of IFN-γ increased in a dose-dependent manner with increasing concentrations of *Daphne kiusiana* extracts (FIG. 6). mRNA of IFN-γ increased remarkably in NK92 cells treated with the *Aleurites fordii* or *Daphne kiusiana* extract (FIG. 7 and FIG. 8). The present inventors found that induction of IFN-γ production by the *Aleurites fordii* extract was reduced in NK92 cells treated with Bay II, and therefore, found that induction of IFN-γ production by the *Aleurites fordii* extract was mediated by NF-κB signaling. That IFN-γ production was reduced with treatment of a PKC signaling pathway inhibitor, rotterin, indicated that upstream signal transduction of NF-κB signaling pathways was induced by the activity of PKC (FIG. 9). As a result of examining the effect of extracts of *Aleurites fordii* or *Daphne kiusiana* on the expressions of cell surface substances in NK92 cells through FACS analysis, expressions of NKG2C and D involving in the activity of NK cells increased remarkably, and expression of NKp44 associated with the natural killing activity of NK cells increased remarkably (FIG. 10). In addition, treating influenza virus-infected A529 cells with the *Aleurites fordii* extract accelerated the increase in expression of IFN-β (FIG. 11). IFN-γ is a cytokine that has a strong macrophage-activating action to be called macrophage-activating factor and has known to produce immune and cellular responses in natural killer (NK) cells. It was found that extracts of *Aleurites fordii* or *Daphne kiusiana* or fractions thereof induce the secretion of IFN-γ, and therefore, have strong antiviral activity.

Therefore, the result suggests that extracts of *Aleurites fordii* or *Daphne kiusiana* or fractions thereof of the present invention can be used effectively for the pharmaceutical composition for the prevention or treatment of viral diseases.

Furthermore, the present invention provides a method for alleviating or treating viral diseases, the method comprising administering a pharmaceutical composition containing a pharmaceutically effective amount of the *Aleurites fordii* or *Daphne kiusiana* extract or the fraction thereof as an active ingredient to an individual having a viral disease.

The present invention also provides a method for preventing viral diseases comprising administering a pharmaceutical composition containing a pharmaceutically effective amount of the *Aleurites fordii* or *Daphne kiusiana* extract or the fraction thereof as an active ingredient to an individual.

The pharmaceutically effective amount may be, but not limited to, from about 0.0001 to about 100 mg/kg, preferably from about 0.001 to about 10 mg/kg. The administration dose may be varied depending on body weight, age, gender, health condition, diet of a certain patient, administration period, administration method, clearance, severity of a disease, etc.

The individual may be vertebrate, preferably mammals, more preferably experimental animals, such as rats, rabbits, guinea pigs, hamsters, dogs, and cats, and most preferably anthropoids, such as chimpanzees and gorillas.

The administration method may be an oral administration or parenteral administration. For parenteral administration, intraperitoneal injection, intrarectal injection, subcutaneous injection, intravenous injection, intramuscular injection, epidural injection in uterine, intracerebrovascular injection, or intrathoracic injection may be selected.

The viral disease may be, but not limited to, a disease infected with one or more viruses selected from the group consisting of Swine Influenza virus (SIV), influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV) and hepatitis virus.

Extracts of *Aleurites fordii* or *Daphne kiusiana*, or fractions thereof of the present invention can induce the secretion of an immune-related cytokine IFN-γ in NK cells, and thus exhibit potent antiviral activity and superior effects for viral diseases, and therefore, can be effectively used for the prevention or treatment of viral diseases.

Furthermore, the present invention provides a healthy food for preventing or alleviating viral diseases containing the *Aleurites fordii* or *Daphne kiusiana* extract or the fraction thereof as an active ingredient.

The viral disease may be, but not limited to, a disease infected with one or more viruses selected from the group consisting of Swine Influenza virus (SIV), influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV) and hepatitis virus.

Extracts of *Aleurites fordii* or *Daphne kiusiana*, or fractions thereof of the present invention may be added intactly or used with other foods or food ingredients and may be used appropriately according to conventional methods.

The healthy food of the present invention may comprise ingredients that are conventionally added for food preparation, for example, proteins, carbohydrates, fats, nutrients, and condiments.

There is no particular limitation as to the kind of food. Examples of foods to which the extract of *Aleurites fordii* or *Daphne kiusiana*, or the fraction thereof can be added include meats, sausages, breads, chocolates, candies, snacks, confectionary, pizzas, instant noodles, other noodles, gum, dairy products including ice creams, a variety of soups, beverages, teas, drinks, alcohol beverages, and vitamin complexes, etc. and include all healthy foods in the conventional meaning.

A healthy beverage composition of the present invention may comprise various flavors or natural carbohydrates, etc. as an additional ingredient like conventional beverages. The natural carbohydrate may be monosaccharides such as glucose and fructose, disaccharides such as maltose and sucrose, polysaccharides such as dextrin and cyclodextrin, and sugar alcohols such as xylitol, sorbitol, erythritol, etc. Natural sweeteners such as thaumatin and stevia extract or synthetic sweeteners such as saccharin and aspartame may used for sweeteners. The amount of the natural carbohydrate may be generally about 0.01 to 0.04 g, preferably about 0.02 to 0.03 g based on 100 mL of the composition of the present invention.

In addition to that, extracts of *Aleurites fordii* or *Daphne kiusiana*, or fractions thereof of the present invention may comprise various nutritional supplements, vitamins, electrolytes, flavors, colorants, pectic acid and its salt, alginic acid and its salt, organic acids, protective colloidal thickeners, pH regulating agents, stabilizers, preservatives, glycerin, alcohols, carbonizing agents used in carbonated drinks, etc. Moreover, extracts of *Aleurites fordii* or *Daphne kiusiana*, or fractions thereof of the present invention may comprise fruit flesh for the preparation of natural fruit juices, fruit juice beverages, and vegetable beverages. These ingredients may be used alone or in combination. Although not critical, these additives are generally used in an amount from about 0.01 to about 0.1 parts by weight, based on 100 parts by weight of the composition of the present invention.

Extracts of *Aleurites fordii* or *Daphne kiusiana*, or fractions thereof of the present invention can induce the secretion of an immune-related cytokine IFN-γ in NK cells, and thus exhibit potent antiviral activity and superior effects for viral diseases, and therefore, can be effectively used for healthy foods for preventing or alleviating viral diseases.

The present invention also provides a feed additive for preventing or alleviating viral diseases containing the *Aleurites fordii* or *Daphne kiusiana* extract or the fraction thereof as an active ingredient.

The viral disease may be, but not limited to, a disease infected with one or more viruses selected from the group consisting of Swine Influenza virus (SIV), influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV) and hepatitis virus.

The feed additive has an antiviral efficacy, and therefore, prevention of viral diseases and alleviation of viral diseases that occurred already can be carried out by feeding steadily the feed additive to poultry, livestock, etc. Feeds may be classed in various ways depending on nutritional value, major ingredients, distribution, water content, mixed condition, and processed form, etc. The feed may be, but not limited to, crude feeds, concentrate feeds, supplemental feeds, proteinous feeds, starchy feeds, fatty feeds, or fibrous feeds.

The feed additive of the present invention may be, but not particularly limited to, composed of 0.1 to 20% by weight of extracts of *Aleurites fordii* or *Daphne kiusiana*, or fractions thereof, 0.001 to 0.01% by weight of lipase, 1 to 20% by weight of tribasic calcium phosphate, 0.01 to 0.1% by weight of vitamin E, 1 to 10% by weight of enzyme powders, 0.1 to 10% by weight of lactobacillus, 0.01 to 10% by weight of a Bacillus culture media, and 20 to 90% by weight of glucose. Any feed additive, provided that it comprises an effective amount of extracts of *Aleurites fordii* or *Daphne kiusiana*, or fractions thereof, may be the feed additive of the present invention.

The effective amount means an amount that allows prevention of viral diseases or alleviation of viral diseases that occurred already, by feeding steadily to poultry, livestock, etc. In addition, the amount that does not produce adverse effects exceeding benefits from the addition of the feed additive is preferable.

In addition, the feed additive may further comprise carriers which are acceptable for poultry, livestock, etc. In the present invention, the feed additive may be used intactly, or well-known carriers, stabilizers, etc. may be added to the feed additive. As necessary, various nutrients such as vitamins, amino acids, minerals, etc., antioxidants, antibiotics, antimicrobials, and other additives may be added. The feed additive may have appropriate formulations, such as powders, granules, pellets, suspensions, etc. The feed additive of the present invention may be provided alone or in a mixture with feeds, for poultry, livestock, etc.

Extracts of *Aleurites fordii* or *Daphne kiusiana*, or fractions thereof of the present invention can induce the secretion of an immune-related cytokine IFN-γ in NK cells, and thus exhibit potent antiviral activity and superior effects for viral diseases, and therefore, can be effectively used for feed additives for preventing or alleviating viral diseases.

Furthermore, the present invention provides a use of the *Aleurites fordii* or *Daphne kiusiana* extract or the fraction thereof for the preparation of a pharmaceutical composition for preventing or treating viral diseases.

The present invention also provides a use of the *Aleurites fordii* or *Daphne kiusiana* extract or the fraction thereof for the preparation of a healthy food for preventing or alleviating viral diseases.

Furthermore, the present invention provides a use of the *Aleurites fordii* or *Daphne kiusiana* extract or the fraction thereof for the preparation of a feed additive for preventing or alleviating viral diseases.

The viral disease may be, but not limited to, a disease infected with one or more viruses selected from the group consisting of Swine Influenza virus (SIV), influenza virus, Influenza A virus subtype H1N1, avian influenza virus, rhinovirus, adenovirus, coronavirus, parainfluenza virus, respiratory syncytial virus, Herpesvirus (HSV), human immunodeficiency virus (HIV) and hepatitis virus.

Extracts of *Aleurites fordii* or *Daphne kiusiana*, or fractions thereof of the present invention can induce the secretion of an immune-related cytokine IFN-γ in NK cells, and thus exhibit potent antiviral activity and superior effects for viral diseases, and therefore, can be effectively used for the preparation of pharmaceutical compositions, healthy foods, or feed additives, for preventing, alleviating, or treating viral diseases.

Hereinafter, the present invention will be described in more detail with reference to the following examples and preparational examples.

However, the following examples and preparational examples are provided for illustrative purposes only, and the scope of the present invention should not be limited thereto in any manner.

EXAMPLE 1

Preparation of Extracts of *Aleurites fordii* and *Daphne kiusiana*

<1-1> Preparation of Methanol Extracts of *Aleurites fordii* Leaves, Stems, and Fruits

*Aleurites fordii* was collected in Seogwipo, Jeju Island, Korea. 4 L of methanol was added to 2 kg of dried leaves, stems, and fruits of *Aleurites fordii*, respectively. Rotary extraction was carried out at room temperature for 24 h and the filtered supernatants were collected. After extraction, the solvent was concentrated under reduced pressure. 276 g of *Aleurites fordii* leaf extract, 120 g of *Aleurites fordii* stem extract, and 100 g of *Aleurites fordii* fruit extract were then obtained.

<1-2> Preparation of Methanol Extracts of *Daphne kiusiana* Leaves, Stems, Flowers, and Roots

*Daphne kiusiana* was collected in Muan, Jeollanam-do, Korea. 4 L of methanol was added to 1 kg of dried leaves, stems, flowers, and roots of *Daphne kiusiana*, respectively. Rotary extraction was carried out at room temperature for 24 h and the filtered supernatants were collected. After extraction, the solvent was concentrated under reduced pressure. 118 g of *Daphne kiusiana* leaf extract, 140 g of *Daphne kiusiana* stem extract, 80 g of *Daphne kiusiana* flower extract, and 105 g of *Daphne kiusiana* root extract were then obtained.

COMPARATIVE EXAMPLE 1

Preparation of Methanol Extract of *Daphne genkwa*

*Daphne genkwa*, which was reported to have an anti-influenza virus activity, (Korean Patent Application No. 10-2009-0034132) was collected in Yongin, Gyeonggi-do, Korea. Methanol extract of *Daphne genkwa* was prepared using dried *Daphne genkwa*, according to the preparation method of extracts in <Example 1>.

EXAMPLE 2

Preparation of Fractions from *Aleurites fordii* Extracts or *Daphne kiusiana* Extracts <2-1> Preparation of *Aleurites fordii* Fractions
<2-1-1> n-Hexane Fractions of *Aleurites fordii*

The respective methanol extracts of *Aleurites fordii* leaves, stems, and fruits obtained in Example <1-1> were suspended in 1.5 L of distilled water and 1.5 L of n-hexane was added to mix. n-Hexane-soluble fractions and water-soluble fractions were separated. This process was repeated three times. The n-hexane soluble fractions were filtered and concentrated under reduced pressure to obtain 27.6 g of *Aleurites fordii* leaf n-hexane fraction, 28 g of *Aleurites fordii* stem n-hexane fraction, and 4 g of *Aleurites fordii* fruit n-hexane fraction.

<2-1-2> Ethylacetate Fractions of *Aleurites fordii*

1.5 L of ethylacetate was added to and mixed with the respective remaining fractions from which n-hexane fractions of *Aleurites fordii* leaves, stems, and fruits were separated in Example <2-1-1>. Ethylacetate fractions were separated. This process was repeated three times. The ethylacetate fractions were filtered and concentrated under reduced pressure to obtain 80 g of *Aleurites fordii* leaf ethylacetate fraction, 18 g of *Aleurites fordii* stem ethylacetate fraction, and 40 g of *Aleurites fordii* fruit ethylacetate fraction.

<2-1-3> Butanol Fractions of *Aleurites fordii*

1.5 L of butanol was added to and mixed with the respective remaining fractions from which ethylacetate fractions of *Aleurites fordii* leaves, stems, and fruits were separated in Example <2-1-2>. Butanol fractions were separated. This process was repeated three times. The butanol fractions were filtered and concentrated under reduced pressure to obtain 55 g of *Aleurites fordii* leaf butanol fraction, 24 g of *Aleurites fordii* stem butanol fraction, and 12 g of *Aleurites fordii* fruit butanol fraction.

<2-2> Preparation of *Daphne kiusiana* Fractions
<2-2-1> n-Hexane Fractions of *Daphne kiusiana* n-Hexane fractions of *Daphne kiusiana* were prepared from the methanol extracts of *Daphne kiusiana* leaves, stems, flowers, and roots obtained in Example <1-2> according to the method described in Example <2-1-1> to obtain 31 g of *Daphne kiusiana* leaf n-hexane fraction, 36 g of *Daphne kiusiana* stem n-hexane fraction, 21 g of *Daphne kiusiana* flower n-hexane fraction, 27 g of *Daphne kiusiana* root n-hexane fraction.

<2-2-2> Ethylacetate Fractions of *Daphne kiusiana*

Ethylacetate fractions of *Daphne kiusiana* were prepared according to the method described in Example <2-1-2> to obtain 7 g of *Daphne kiusiana* leaf ethylacetate fraction, 8.4 g of *Daphne kiusiana* stem ethylacetate fraction, 5 g of *Daphne kiusiana* flower ethylacetate fraction, 6 g of *Daphne kiusiana* root ethylacetate fraction.

<2-2-3> Butanol Fractions of *Daphne kiusiana*

Butanol fractions of *Daphne kiusiana* were prepared according to the method described in Example <2-1-3> to obtain 20 g of *Daphne kiusiana* leaf butanol fraction, 24 g of *Daphne kiusiana* stem butanol fraction, 14 g of *Daphne kiusiana* flower butanol fraction, 18 g of *Daphne kiusiana* root butanol fraction.

EXAMPLE 3

Examination of the Interferon-γ (IFN-γ) Secretion-inducing Activity of Extracts of *Aleurites fordii* or *Daphne kiusiana*, or Fractions Thereof <3-1> Natural Killer (NK) Cell Culture The interleukin-2 (IL-2)-dependent natural killer (NK) cell line NK92 (human NK lymphoma) was purchased from American Type Culture Collection (ATCC). NK92 cells were cultured in α-MEM (α-minimal essential medium) (Life Technologies, Karlsruhe, Germany) containing 20% fetal calf serum (FCS) (HyClone, Logan, Utah), 2 mM L-glutamate, 100 μg/mL penicillin, 100 μg/mL streptomycin (Life Technologies), and supplemented with 100 U/mL IL-2 (Chiron, Emeryville, Calif.) at 37° C., 5% $CO_2$.

<3-2> Examination of the Interferon-γ (IFN-γ) Secretion-inducing Activity of Extracts of *Aleurites fordii* or *Daphne kiusiana*, or Fractions Thereof Through Enzyme-linked Immunosorbent assay (ELISA)

2 μg/mL of each extract of *Aleurites fordii* leaves, stems, or fruits or each fraction thereof (n-hexane fractions, ethylacetate fractions, butanol fractions, or water fractions), or each extract of *Daphne kiusiana* leaves, stems, flowers, or roots, or each fraction thereof was treated to the culture media of NK92 cells incubated according to Example <3-1>, and incubated at 37° C. for 18 h, and then, NK cells were removed to obtain supernatants. For quantification of human IFN-γ present in the culture media of NK92 cells, enzyme-linked immunosorbent assay (ELISA) was carried out using a commercially available monoclonal antibody (mAb) (Endogen) according to manufacturer's instructions. *Daphne genkwa* extract and dimethylsulfoxide (DMSO) were used for positive control (PC) and negative control (NC), respectively. Quantitative value of IFN-γ was represented as the mean±standard deviation from three replicate analyses.

Figure 2:
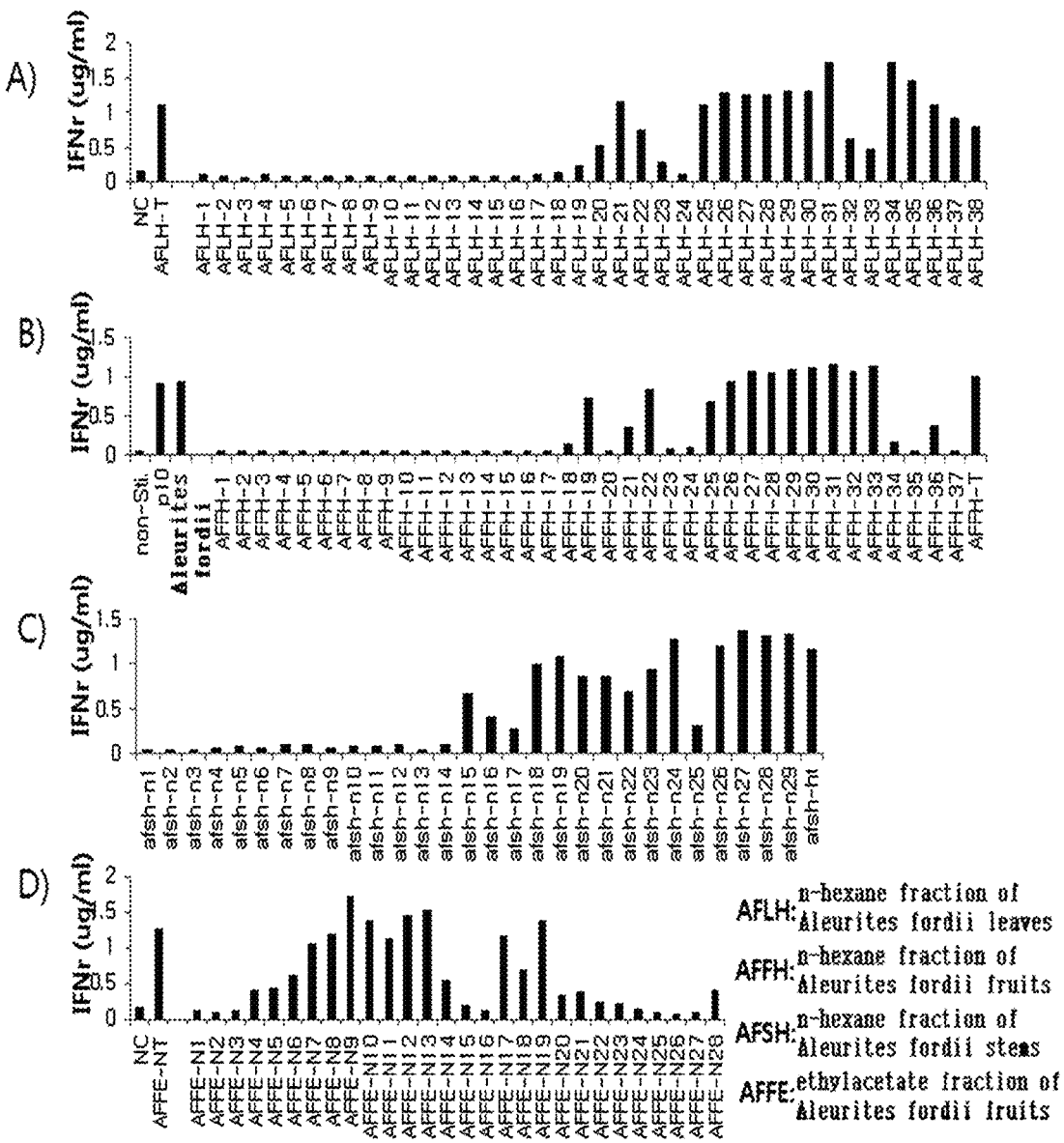
FIG. 2 is graphs showing the result of analyzing IFN-γ secretion in NK92 cells treated with each fraction fractionated from each extract of leaves, stems, and fruits of *Aleurites fordii*:
  A: n-hexane fraction of *Aleurites fordii* leaves;
  B: n-hexane fraction of *Aleurites fordii* fruits;
  C: n-hexane fraction of *Aleurites fordii* stems; and
  D: ethylacetate fraction of *Aleurites fordii* fruits.

Consequently, for extracts of *Aleurites fordii* or fractions thereof, as shown in Table 1 and FIG. 1, NK92 cells treated with each methanol extract of *Aleurites fordii* leaves, stems, or fruits secreted about 1.7 to 2.0 ng/mL of IFN-γ. When NK92 cells were treated with organic solvent fractions excluding water layers (n-hexane fractions, ethylacetate fractions, or butanol fractions), fractions of extracts of *Aleurites fordii* leaves, stems, or fruits, NK92 cells treated with n-hexane fractions secreted about 1.7 to 2.1 ng/mL of IFN-γ; NK92 cells treated with ethylacetate fractions secreted about 1.5 to 2.0 ng/mL of IFN-γ; and NK92 cells treated with butanol fractions secreted about 1.2 to 1.7 ng/mL of IFN-γ. NK92 cells treated with *Aleurites fordii* water fractions secreted about 0.3 to 0.4 ng/mL that was significantly small amount of IFN-γ compared to *Aleurites fordii* extracts or organic solvent fractions, and therefore, *Aleurites fordii* water fractions have little ability to secrete IFN-γ. All NK92 cells treated with extracts of *Aleurites fordii* or fractions thereof secreted significantly greater amount of IFN-γ compared to negative control (0.3 ng/mL) (Table 1 and FIG. 1). As shown in FIG. 2, the effect to secrete IFN-γ of fractions of extracts of *Aleurites fordii* leaves, stems, or fruits was confirmed (FIG. 2). Therefore, the result indicated that extracts of *Aleurites fordii* leaves, stems, or fruits, or fractions thereof have the activity to induce IFN-γ secretion in NK cells.

Meanwhile, for extracts of *Daphne kiusiana* or fractions thereof, as shown in Table 2 and FIG. 3, NK92 cells treated with each methanol extract of *Daphne kiusiana* leaves, stems, flowers, or roots secreted about 2.4 to 2.6 ng/mL of IFN-γ. When NK92 cells were treated with organic solvent fractions excluding water layers (n-hexane fractions, ethylacetate fractions, or butanol fractions), fractions of extracts of *Daphne kiusiana* leaves, stems, flowers, or roots, NK92 cells treated with n-hexane fractions secreted about 1.7 to 1.8 ng/mL of IFN-γ; NK92 cells treated with ethylacetate fractions secreted about 1.4 to 1.8 ng/mL of IFN-γ; and NK92 cells treated with butanol fractions secreted about 1.6 to 1.9 ng/mL of IFN-γ. NK92 cells treated with *Daphne kiusiana* water fractions secreted about 0.2 to 0.4 ng/mL of IFN-γ, and therefore, *Daphne kiusiana* water fractions have little ability to secrete IFN-γ. All NK92 cells treated with extracts of *Daphne kiusiana* or fractions thereof secreted significantly greater amount of IFN-γ compared to negative control (0.3 ng/mL) (Table 2 and FIG. 3). As shown in FIG. 4, the effect to secrete IFN-γ of fractions of extracts of *Daphne kiusiana* leaves, stems, flowers, or roots was confirmed (FIG. 4). Therefore, the result indicated that extracts of *Daphne kiusiana* leaves, stems, flowers, or roots, or fractions thereof stimulate IFN-γ secretion in NK cells.

TABLE 1

| Sample (2 µg/mL) | | IFN-γ secretion (ng/mL) |
|---|---|---|
| *Aleurites fordii* leaves | Methanol extract | 1.7 |
| | n-Hexane fraction | 2.0 |
| | Ethylacetate fraction | 1.5 |

TABLE 1-continued

| Sample (2 µg/mL) | | IFN-γ secretion (ng/mL) |
|---|---|---|
| | Butanol fraction | 1.2 |
| | Water fraction | 0.4 |
| *Aleurites fordii* stems | Methanol extract | 2.0 |
| | n-Hexane fraction | 2.1 |
| | Ethylacetate fraction | 1.9 |
| | Butanol fraction | 1.7 |
| | Water fraction | 0.3 |
| *Aleurites fordii* fruits | Methanol extract | 2.0 |
| | n-Hexane fraction | 1.7 |
| | Ethylacetate fraction | 2.0 |
| | Butanol fraction | 1.7 |
| | Water fraction | 0.3 |
| *Daphne genkwa* | Methanol extract (Positive control) | 2.0 |
| DMSO | Negative control | 0.3 |

TABLE 2

| Sample (2 µg/mL) | | IFN-γ secretion (ng/mL) |
|---|---|---|
| *Daphne kiusiana* leaves | Methanol extract | 2.5 |
| | n-Hexane fraction | 1.7 |
| | Ethylacetate fraction | 1.4 |
| | Butanol fraction | 1.6 |
| | Water fraction | 0.4 |
| *Daphne kiusiana* stems | Methanol extract | 2.6 |
| | n-Hexane fraction | 1.8 |
| | Ethylacetate fraction | 1.7 |
| | Butanol fraction | 1.8 |
| | Water fraction | 0.5 |
| *Daphne kiusiana* flowers | Methanol extract | 2.4 |
| | n-Hexane fraction | 1.8 |
| | Ethylacetate fraction | 1.7 |
| | Butanol fraction | 1.7 |
| | Water fraction | 0.3 |
| *Daphne kiusiana* roots | Methanol extract | 2.4 |
| | n-Hexane fraction | 1.7 |
| | Ethylacetate fraction | 1.8 |
| | Butanol fraction | 1.9 |
| | Water fraction | 0.3 |
| *Daphne genkwa* | Methanol extract (Positive control) | 2.0 |
| DMSO | Negative control | 0.3 |

<3-3> Determination of the Activity to Induce Interferon-γ (IFN-γ) Secretion of *Aleurites fordii* or *Daphne kiusiana* Extracts at Different Concentrations Through ELISA The amount of IFN-γ secretion was measured at different concentrations of methanol extracts of *Aleurites fordii* leaves, stems, and fruits; methanol extracts of *Daphne kiusiana* by the method in Example <3-2>. Concentrations of methanol extracts were 0.01, 0.1, 1, or 10 µg/mL.

Consequently, as shown in FIG. 5, methanol extract of *Aleurites fordii* leaves increased IFN-γ secretion significantly at 1 µg/mL or higher concentrations, and methanol extracts of *Aleurites fordii* stems and fruits increased IFN-γ secretion drastically at 10 µg/mL of concentration (FIG. 5). As shown in FIG. 6, methanol extracts of *Daphne kiusiana* increased IFN-γ secretion remarkably at 1 µg/mL or higher concentrations (FIG. 6). Therefore, it was confirmed that the secretion of IFN-γ increases in a dose-dependent manner with increasing concentrations of *Aleurites fordii* or *Daphne kiusiana* methanol extracts.

<3-4> Effect of Extracts of *Aleurites fordii* or *Daphne kiusiana* or Fractions Thereof on the Expression of Genes Involved in the Induction of IFN-γ Secretion RT-PCR was carried out to investigate changes in expression of mRNAs involved in IFN-α and IFN-γ induction in NK92 cells. NK92 cells or lung epithelial A549 cells were incubated with 2 ng of the *Aleurites fordii* extract or *Daphne kiusiana* extract for 12 h. At 15 min, 30 min, 45 min, 1 h, 4 h, and 12 h after incubation, cells were lysed, RNAs were isolated according to a well-known protocol, and IFN-γ mRNA expression was analyzed through RT-PCR. Primers for IFN-γ used herein were as follows: forward primer was 5'-TCCCATGGGTTGTGTGTTTA-3'(SEQ ID NO:1); reverse primer was 5'-GTCAGGGTGCAGCCGG-3'(SEQ ID NO:2). GAPDH were used as an internal standard and primers for GAPDH used herein were as follows: forward primer was 5'-CCATCACCATCTTCCAGGAG-3'(SEQ ID NO:3); reverse primer was 5'-ACAGTCTTCTGGGTGGCAGT-3' (SEQ ID NO:4).

The above RT-PCR was carried out with the above primer pairs and Taq polymerase (Takara, Shiga, Japan). Whole RNAs were isolated according to a standard protocol, and cDNA was synthesized using AccuScript High Fidelity 1$^{st}$ Strand cDNA Synthesis Kit (Stratagene) according to manufacturer's instructions. 1 μL of cDNA was used for 20 μL of PCR consisting of 0.5 U ExTaq DNA polymerase, 1× buffer, 1 mM dNTP mix (Takara), and the above primer pairs. PCR amplification was carried out using GeneAmp PCR system 2700 (Applied Biosystems, Foster city, CA, USA) under the following condition: 94° C. for 5 min; 25 to 40 cycles of 94° C. for 45 sec, 56° C. for 45 sec, and 72° C. for 1 min; final extension of 72° C. for 7 min. PCR primers were designed using Primer3 program and purchased from Bioneer (Daejeon, South Korea). PCR products were separated on 1.5% agarose gel, stained with ethidium bromide (EtBr), visualized with Gel Doc 2000 UV trans-illuminator (Bio-Rad Laboratories, Hercules, Calif., USA), and analyzed using Quantity One software (Bio-Rad Laboratories). Each sample was tested three times or more, and representative data were shown.

Consequently, as shown in FIG. 7, IFN-γ transcriptome increased remarkably in NK92 cells treated with the *Aleurites fordii* extract after 2 h, and this suggested that the reaction for inducing IFN-γ for the *Aleurites fordii* extract was induced within 1 to 2 h at a transcription level (FIG. 7). Meanwhile, as shown in FIG. 8, expressions of IFN-γ mRNA and IFN-α mRNA in NK92 cells and lung epithelial A549 cells which were treated with *Daphne kiusiana* were determined at different time, and consequently, IFN-γ transcriptome increased remarkably in NK92 cells treated with the *Daphne kiusiana* extract after 3 h, and this suggested that the reaction for inducing IFN-γ for the *Daphne kiusiana* extract was induced within 3 h at a transcription level. The *Daphne kiusiana* extract increased the expression of IFN-α mRNA in A549 cells (FIG. 8).

EXAMPLE 4

Examination on Dependence of IFN-γ Production-inducing Effect of *Aleurites fordii* Extract on NF-κB Signaling Pathways To prove that the IFN-γ production-inducing effect of the *Aleurites fordii* extract is dependent on NF-κB signaling pathways, NK92 cells were treated with an NF-κB inhibitor Bay II or a PKC signaling pathway inhibitor Rotterin along with the *Aleurites fordii* extract.

Consequently, as shown in FIG. 9, induction of IFN-γ production by the *Aleurites fordii* extract was reduced in NK92 cells treated with Bay II in a dose-dependent manner with increasing concentrations of Bay II. Therefore, this suggested that induction of IFN-γ production by the *Aleurites fordii* extract was mediated by NF-κB signaling. That IFN-γ production was reduced with treatment of a PKC signaling pathway inhibitor, rotterin, indicated that upstream signal transduction of NF-κB signaling pathways was induced by the activity of PKC (FIG. 9).

EXAMPLE 5

Examination on Effect of *Aleurites fordii* or *Daphne kiusiana* Extracts on Cell Surface Substances Fluorescence activated cell sorter (FACS) analysis was carried out to examine changes in cell surface substances involving in the activity of NK92 cells treated with *Aleurites fordii* extract or *Daphne kiusiana* extract. Expressions of cell surface substances NKG2A, C, and D, which function as active ligands for NK cells; and NKp30, NKp44, and NKp46, which involve in natural killing activity were analyzed.

Consequently, as shown in FIG. 10, *Aleurites fordii* extract and *Daphne kiusiana* extract exhibited similar aspects of cell surface substances expression in NK92 cells, and expressions of NKG2C and D involving in the activity of NK cells increased remarkably, and expression of NKp44 associated with the natural killing activity of NK cells increased remarkably (FIG. 10).

EXAMPLE 6

Examination on Effects of *Aleurites fordii* Extract on Virus-infected Lung Epithelial Cell Line To examine effects of the *Aleurites fordii* extract on influenza virus-infected cells, influenza virus-penetrated lung epithelial cell line, A549 cells were treated with the *Aleurites fordii* extract, and RT-PCR was carried out by the method in Example <3-4> to examine IFN-α and IFN-β transcription activities.

Consequently, as shown in FIG. 11, expressions of IFN-α and IFN-β appeared in influenza virus-treated A549 cells after 24 h, and treating influenza virus-infected A529 cells with the *Aleurites fordii* extract decreased the amount of IFN-α expression and accelerated the increase in IFN-β expression (FIG. 11).

As stated above, extracts of *Aleurites fordii* or *Daphne kiusiana* or fractions thereof of the present invention exhibit excellent antiviral activity, and therefore, can be effectively used for the development of drugs for the prevention and treatment of viral diseases or healthy foods and feed additives for the prevention and alleviation of viral diseases, and research on methods for preventing or treating viral diseases using these drugs, foods, and feed additives.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for alleviating or treating viral disease, wherein the viral disease is an influenza virus infection, comprising administering a pharmaceutically effective amount of *Aleurites fordii* extract or a fraction thereof to an individual having the viral disease.

2. The method as set forth in claim 1, wherein the *Aleurites fordii* extract is prepared by extracting a dry matter of *Aleurites fordii* with water, a lower alcohol of $C_1$ to $C_2$, or a mixture thereof.

3. The method as set forth in claim 2, wherein the dry matter of *Aleurites fordii* is leaves, stems, or fruits of *Aleurites fordii*.

4. The method as set forth in claim 2, wherein the extract is prepared by extracting the dry matter with ethanol or methanol.

5. The method as set forth in claim 1, wherein the *Aleurites fordii* fraction is an organic solvent fraction which is prepared by further extracting the *Aleurites fordii* extract with an organic solvent.

6. The method as set forth in claim 5, wherein the organic solvent is hexane, ethylacetate, or butanol.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: interferon-gamma forward primer

<400> SEQUENCE: 1
tcccatgggt tgtgtgttta                                           20

<210> SEQ ID NO 2
<211> LENGTH: 16
<212> TYPE: DNA
<213> ORGANISM: Artificial Sequence
<220> FEATURE:
<223> OTHER INFORMATION: interferon-gamma reverse primer

<400> SEQUENCE: 2
gtcagggtgc agccgg                                               16

<210> SEQ ID NO 3
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 3
ccatcaccat cttccaggag                                           20

<210> SEQ ID NO 4
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 4
acagtcttct gggtggcagt                                           20
```